United States Patent [19]

Brown et al.

[11] 4,284,553

[45] Aug. 18, 1981

[54] REVERSIBLE METHOD FOR COVALENT IMMOBILIZATION OF BIOCHEMICALS

[75] Inventors: Rodney J. Brown, Logan, Utah; Harold E. Swaisgood; Horace R. Horton, both of Raleigh, N.C.

[73] Assignee: North Carolina State University at Raleigh, Raleigh, N.C.

[21] Appl. No.: 161,645

[22] Filed: Jun. 20, 1980

[51] Int. Cl.³ .......................... C09C 3/08; C09C 3/10; C09C 3/12; C12N 9/96
[52] U.S. Cl. ............................ 260/112 R; 106/308 B; 106/308 Q; 260/112 B; 260/112.5 R; 435/188; 427/220
[58] Field of Search ............ 260/112 R, 112.5, 112 B; 435/188; 106/308 Q, 308 B; 427/220

[56] References Cited

U.S. PATENT DOCUMENTS 4,043,871  8/1977  Blixt et al. .................. 106/308 Q X
4,068,024  1/1978  Laufer ........................ 106/308 Q X

OTHER PUBLICATIONS

Nature, Cuatrecasas, vol. 228, pp. 1327–1328, (1970).
Methods in Enzymology, vol. 44, 1976, pp. 516–527, (1976).
Fed. Proc., 32, p. 496, (1973), Brown et al.
Biochemistry, 15, pp. 4215–4222, Chan et al., (1976).
Biochem. Biophys. Res. Comm., 48, pp. 1068–1073, Brown et al., (1972).
Biochim-Biophysica Acta, 334, pp. 243–256, Cho et al., (1974).

*Primary Examiner*—Howard E. Schain
*Attorney, Agent, or Firm*—Cushman, Darby & Cushman

[57] ABSTRACT

A method for the reversible immobilization of proteins through covalent attachment to inorganic oxide surfaces, such as glass or silica, via thioester containing coupling chains. Resulting succinamidopropyl-surfaces are converted into the acyl derivative using anhydrous thionyl chloride, and then treated with either 3-mercaptopropionic acid or mercaptoacetic acid. Thus derivatized, the material is dried, and can be stored for extended periods of time without detectable loss of reactivity with proteins. Immobilization of proteins can be readily achieved simply by suspending the derivatized material in buffer (pH=5 to 8) and recycling the protein solution through the material. Following immobilization, protein molecules can be released from the surface by cleavage of the coupling chains at the thioester linkage through treatment with hydroxylamine.

10 Claims, 4 Drawing Figures

REVERSIBLE METHOD FOR COVALENT IMMOBILIZATION OF BIOCHEMICALS

BACKGROUND OF THE INVENTION

The present invention provides a means for immobilizing proteins through covalent attachment to inorganic oxide surfaces via thioester-containing coupling chains. Once immobilized, the protein can be released from the surface by cleavage of the coupling chains at the thioester linkage.

Covalent coupling of proteins to solid supports generally relies on common organic reactions. Most of the methods which have been used were reviewed by Mosbach, K., Ed. (1976), *Methods Enzymol.* 44, Academic Press, New York or by Zaborsky, O. (1973), *Immobilized Enzymes*, CRC Press, Cleveland, Ohio.

Generally, characterization of immobilized enzymes has been limited to kinetic studies or to examination of fluorescent spectra (see Gable, D., Steinberg, I. Z., and Katchalski, E. (1971), *Biochemistry* 10, 4661-4669; Horton, H. R., and Swaisgood, H. E. (1976), *Methods Enzymol.* 44, 516-526; and Swaisgood, H. E., Janolino, V. G., and Horton, H. R. (1978), *Arch Biochem. Biophys.* 191, 259-268). This restriction severely limits the application of immobilization techniques for studies of the reformation of the tertiary structure or quaternary structure in proteins. However, the capability of selectively releasing an immobilized protein following various experimental operations would allow the application of many additional biochemical techniques for examination of structural features.

One of the problems often encountered in studies of immobilized enzymes is elucidation of the factors involved in altered kinetic patterns. The catalytic rates of enzymes may be affected in several ways by immobilization: (1) by changes in specific rate constants as a result of conformational changes in the enzyme's structure per se, alteration of its micro-environment, or steric hindrance of substrate access; (2) by partitioning of solute molecules (including substrates and products) due to specific interactions with the matrix; and (3) by diffusion inhibition (see Engasser, J. M., and Horvath, C. (1973). *J. Theor. Biol.* 42, 137-155; Goldstein, L. (1976), *Methods Enzymol.* 44, 397-443; Kobayashi, T., and Laidler, K. J. (1973), *Biochim. Biophys. Acta* 302, 1-12 and Cho, I. C., and Swaisgood, H. (1974), *Biochim. Biophys. Acta* 334, 243-256). It has been very difficult to distinguish among these various kinetic effects while an enzyme remains immobilized.

Removal of an immobilized enzyme from its supporting matrix in such a way as to retain a portion of the chain involved in the previous covalent attachment would provide a feasible means for investigation of conformational changes or steric hindrance directly related to the immobilization procedure. Also, the effect of the microenvironment of the matrix surface, itself, could be thus eliminated, so that the effects of partitioning and diffusion can be clearly separated experimentally from intrinsic changes in specific rate constants.

The possibility of releasing protein immobilized through an azo linkage with sodium dithionite or of releasing thioester-linked protein with hydroxylamine or high pH had been suggested by Cuatrecasas, P. (1970a), *Nature* 228, 1327-1328. More recently, Chan, W. W. C., and Mosbach, K. (1976), *Biochemistry* 15, 4215-4222 have reported a procedure for reversible immobilization based on a disulfide linkage. An attempt to form a selectively cleavable covalent bond, by incorporating a thioester linkage, was reported by Brown, J. C., and Horton, H. R. (1973), *Fed. Proc.* 32, 496. Carbodiimide-activated succinylated glass beads (Brown, J. C., Swaisgood, H. E., and Horton, H. R. (1972), *Biochem. Biophys. Res. Commun.* 48, 1068-1073) were treated with 2-mercaptoacetic acid; the derivatized glass was then treated with 1-ethyl-3-(3-dimethylaminopropyl)-carbodiimide (EDC), and finally exposed to the protein-containing solution. Subsequently, immobilized protein could be removed from the glass surface by cleaving the thioester bonds with hydroxylamine, but the yield of released protein was low (approximately 15% of that immobilized).

Thus, many methods for covalent immobilization of biochemicals have been described as noted above. However, for most of these methods the immobilized molecule, especially enzymes or proteins, can not be released without destruction of its integrity. The only reported method for reversible covalent attachment of molecules to surfaces involve linkage through disulfide bonds. However, these linkages would not be stable in the presence of mild reducing agents. Such agents are often required for the maintenance of biological activity.

An ideal method for reversible covalent immobilization would have the following characteristics:

1. The activated form of the particles used for immobilization should be very stable so that such particles could be shipped and stored until immobilization of a biochemical is desired.
2. The immobilization should be accomplished simply by addition a solution containing the biochemical.
3. The chemistry of immobilization should not affect the biological activity of the molecule.
4. The immobilization method should achieve maximum loading of the particle surface area with the biochemical.
5. The covalent chain linking the biochemical to the surface should be stable under most conditions so that the biochemical is not slowly leached from the surface.
6. The covalent chain linking the biochemical to the particle surface should be cleaved by specific reagents under very mild conditions so as not to alter the biological activity of the released biochemical.

Accordingly, it is the primary object of the present invention to provide a method for the immobilization of proteins which to a large degree meets the ideal immobilization procedure noted above.

It is a further object of the present invention to provide a relatively simple method for immobilization of proteins while at the same time achieving a high degree of loading and biological activity of the immobilized protein.

These and other objects of the present invention will become apparent from the discussion which follows.

SUMMARY OF THE INVENTION

We have discovered a new method for covalent immobilization which allows for subsequent release of the protein by very mild treatment with hydroxylamine. Furthermore, in contrast with immobilization by formation of a mixed disulfide as described by Chan, W. W. C., and Mosbach, K. (1976), *Biochemistry* 15, 4215-4222, the procedure described herein provides a covalent linkage between the protein and the matrix which is stable in the presence of thiols, a feature of considerable importance when one wishes to examine the acquisition of disulfide bond-containing tertiary structures or protect the biological activity of sulfhydryl-containing proteins.

The present invention provides a technique for the treatment of inorganic oxide materials to provide an activated surface thereon suitable for the reversible immobilization of proteins.

For the purpose of this application, it is to be understood that "inorganic oxide materials" refers to any material having an inorganic oxide surface capable of reacting to form a bond with triethoxyaminopropyl silane. Particularly suitable are siliceous materials such as porous silica and porous glass beads. However, other materials may also be employed such as aluminum oxide, aluminum-silicates, etc.

As used herein, the term "activated surface" is to be understood as a surface, containing a thioester linkage, which is capable of forming a covalent bond with compounds having a free amino group.

The term "protein" as used herein is defined as organic compounds possessing a free amino group capable of forming a covalent bond with the activated surface. Thus, protein is inclusive of enzymes, amino acids and like materials.

The reversible method for the covalent immobilization of proteins in accordance with the invention comprises the steps of:
 a. treating an inorganic oxide material to provide an activated surface thereon; and
 b. contacting the activated surface with protein having a reactive amino group whereby said protein is covalently bonded to the activated surface.

Treating of the inorganic oxide material to provide an activated surface thereon is carried out by:
 a. silanizing and succinylating an inorganic oxide material to provide a succinamidopropyl-surface;
 b. converting the succinamidopropyl-surface to the acyl chloride derivative by treatment under anhydrous conditions;
 c. reacting the acyl chloride derivative with either 3-mercaptopropionic acid or mercaptoacetic acid under anhydrous conditions whereby the surface of the material is activated; and
 d. drying the activated material.

The silanizing and succinylating is carried out according to known procedures. Thus, silanizing is accomplished generally by treating the inorganic oxide material with an aqueous solution (e.g. about 10%) of the triethoxyaminosilane at a pH of about 4. Thereafter, succinylating is accomplished by treating the material with either an aqueous solution of succinic anhydride at a pH of about 6, or an aqueous solution of succinic acid and carbodiimide.

Formation of the acyl derivative is accomplished by reaction with thionyl chloride dissolved in an inert organic solvent (e.g. methylene chloride) in the absence of water, i.e. under anhydrous conditions.

At this point, the acyl derivative is reacted with either mercaptopropionic acid or mercaptoacetic acid dissolved in an inert organic solvent such as methylene chloride in the absence of water. Upon completion of the reaction, the material is dried, in vacuo, and stored.

We have also found that this derivative exhibits some unexpected chemical properties in that the terminal carboxyl group is now very reactive with nucleophiles, i.e. free amino groups, such as the ε-amino group of lysyl residues or the terminal α-amino group of proteins, amino acids, or peptides. This is a surprising and unexpected result of our invention, since, heretofore it was thought that the acid derivative must be activated by treatment with carbodiimide, but we have found such treatment unnecessary. Based on a number of observations we propose the following chemistry.

The thioester derivative may be washed with water, dried, and stored for long periods of time without losing its ability to covalently immobilize protein without further chemical treatment.

Immobilization is accomplished by simply adding a solution of the protein at a pH around neutrality to e.g. dry glass beads. Hence, the procedure is as simple and mild as one could possibly imagine. The loadings and biological activities obtained for various enzymes and antibodies using this procedure is as good or better than those reported for other methods. Furthermore, the immobilized proteins are quite stable with respect to leaching. For example, essentially no protein loss occurred during long periods of storage or in the presence of high concentrations of protein denaturants such as guanidinium chloride or urea. The latter observations show conclusively that the immobilization is covalent.

Release of the immobilized biochemical can be achieved also under very mild conditions by the specific reagent hydroxylamine at room temperature. This reagent specifically cleaves the thioester bond, the proposed chemistry being:

Our data show that the biological activity of enzymes is not affected by this release procedure. Furthermore, the number of attachment sites and the location can be determined since the released protein is now labelled by the addition of a thiol group. This result can be extremely useful for many types of biochemical investigations.

DETAILED DESCRIPTION OF THE INVENTION

The amount of protein which can be immobilized using our procedure, viz. 10–20 mg/g, is comparable to that attainable by other, commonly used methods such as Mosbach, K., Ed. (1976), *Methods Enzymol.* 44, Adademic Press, New York, and to that obtained in using carbodiimide activation of succinamidopropyl-glass as described by Cho, I. C., and Swaisgood, H. (1974), *Biochim. Biophys. Acta* 334, 243–256 and Horton, H. R., and Swaisgood, H. E. (1976), *Methods Enzymol.* 44, 516–526. Accepting the value for total surface area supplied by the manufacturer, 50 m$^2$/g, an area of 94 A$^2$ for each site can be estimated from our data. Assuming an even distribution of protein molecules on the surface and a diameter for α-chymotrypsin of 40 A, protein molecules would be separated by roughly two diameters at a level of loading of 20 mg/g; lower levels of loading would result in proportionately greater intermolecular distances.

An additional versatility of our method is provided by the potential for subsequent release of immobilized protein, also under very mild conditions, due to the susceptibility of thioester bonds to hydroxylaminolysis. Over half the protein immobilized could be released simply by washing with 1 M hydroxylamine at room temperature and pH 7.0. Such treatment did not affect the activity of native α-chymotrypsin. Another important feature of this release process is that sulfhydryl group(s) remain associated with the protein, one for each site which has been bound to the matrix via a thioester linkage. This provides an easy means of measuring the number of binding sites per molecule of protein, especially in proteins with no naturally occurring free sulfhydryl groups. This "tagging" procedure could also be useful for chemically determining the specific site(s) of reaction within protein chains.

Figure 4:
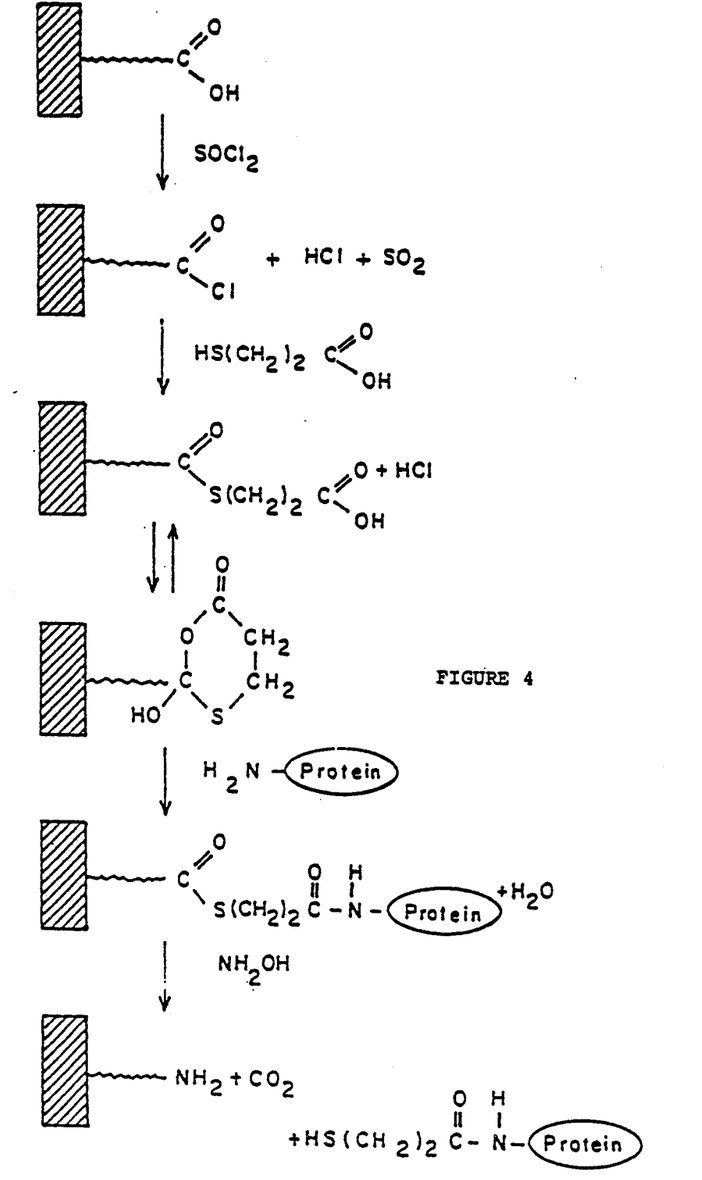
FIG. 4 shows proposed reactions for the formation of the thioester-glass derivative, its reaction with protein, and release of the immobilized protein by hydroxylaminolysis.

FIG. 4 presents a postulated reaction sequence for immobilization and release based on the following observations: (1) mass spectra indicated that S-succinyl-mercaptopropionic acid chains were attached to the aminopropyl derivative as expected from well known organic reactions; (2) only those model compounds having free amino groups were immobilized to the derivatized beads; (3) catalytically active protein was released by hydroxylamine which has a demonstrated specificity for thioesters as described by Bruice, T. C. (1961), in *Organic Sulfur Compounds* (Kharasch, N., Ed.) Vol. I, pp 421–442, Pergamon Press, New York; and (4) the released α-chymotrypsin contained free sulfhydryl groups whereas none are present in the native enzyme. To explain the unanticipated reactivity of the thioester-glass derivative, the formation of a ring is suggested, as shown in the figure. Construction of space-filling models indicates that such a ring (five- or six-membered) is sterically possible for each of the two mercaptoacids used. It is postulated that formation of the ring creates an anhydride-like derivative, thereby increasing the susceptibility of the terminal "carboxyl group" to nucleophilic attack. With a lower pK$_a$ and, hence, greater nucleophilicity of the α-amino group under the conditions employed, somewhat greater immobilization of glycine ethyl ester occured than of the lysyl derivative (via its ε-amino group). Above pH 8, the glass-bound derivative loses it reactivity, possibly due to hydrolysis of the ring. Incomplete release of protein in hydroxylamine could result either from a limited extent of hydroxylaminolysis of the thioester bonds or from initial partitioning of nucleophilic attack by the protein on the carbon in the thioester bond as well as the terminal carbon during the immobilization procedure.

Hydroxylaminolysis of the thioester bond in the coupling chain of the immobilized protein yields the thioacylated protein and the corresponding hydroxamic acid derivative. The latter may undergo a Lossen rearrangement giving the isocyanate which, upon hydrolysis, would yield the amine and CO$_2$. Such reaction could be the basis for the observed evolution of gas during the release reaction.

The decrease in the amount of protein immobilized upon treatment of the thioester derivative with carbodiimide may also be due to ring formation. If some of the mercapto acid was displaced by carbodiimide, forming the O-acrylisourea derivative at that point in the chain, subsequent reaction with protein would yield immobilized protein which would not be susceptible to release by hydroxylamine; such decreased release was observed (See Table I below). The fact that less protein was immobilized may be due to the time which elapsed between treatment with carbodiimide and exposure to the protein, during which partial hydrolysis of the O-acrylisourea probably occurred.

Several studies have been reported in which attempts were made to examine experimentally the effect of the chemical attachment of the coupling chain on enzyme activity. In all of the cases, soluble enzymes were treated with soluble reagents under conditions as similar as possible to those used for immobilization. Thus, Swaisgood, H., and Natake, M. (1973), *J. Biochem. (Tokyo)* 74, 77–86 found a linear relationship between the activity remaining and the number of glycine methyl ester residues incorporated onto carboxyl side chains of glutamate dehydrogenase using carbodiimide-activation of the protein's carboxyl groups. These authors also found subtle changes in the kinetic behavior of enzyme preparations which had only 3–4 modified residues per subunit. Cho, I. C., and Swaisgood, H. (1974), *Biochim. Biophys. Acta* 334, 243–256 compared the kinetics of native lactate dehydrogenase with those of soluble enzyme containing an average of five modified carboxyl groups and enzyme which had been immobilized to aminopropyl-glass using similar reaction conditions. In that case, the kinetic parameters of the native and the soluble, modified enzyme were essentially the same. Later, Ollis, D. F., and Datta, R. (1976) *Methods Enzymol.* 44, 444–450 compared derivatized soluble forms and similarly immobilized forms of lysozyme, lipase, and α-chymotrypsin. They found α-chymotrypsin to be less sensitive to modification, but in all three cases high degrees of modification were logarithmically related to loss of activity.

The method of the present invention has the distinct advantage that there is no question about the chemical identity of the derivatized functional groups of modified, soluble and immobilized enzyme preparations. Kinetic parameters for the hydroxylamine-released α-chymotrypsin derivative, which had an average of about three chains incorporated per molecule, were essentially the same as those for native enzyme. Hence, the observed kinetic differences between the immobilized enzyme and soluble enzyme must be attributed to effects of diffusion and, possibly, partitioning of substrates, products, etc.

The ability to remove a portion of the immobilized enzyme by hydroxylamine-treatment also allows comparison of the kinetics of the same immobilized preparation at two levels of enzyme loading. Hence, the intrinsic $K_m$ values, particle radii, and $D_{eff}$ should be identical for a sample of immobilized enzyme before and after partial release of enzyme. Consequently, the method for assessing the effect of diffusion, suggested by Engasser, J. M., and Horvath, C. (1973), *J. Theor. Biol.* 42, 137–155 (the contents of which are incorporated herein by reference) should be directly applicable to the present derivatives, and some of the problems inherent in comparisons of different preparations should be avoided. The only quantity required by this method which is not available by direct measurement from our data is $V_{max}'$, since sufficiently high substrate concentrations to allow this extrapolation were not accessible. Nevertheless, a good approximation can be obtained from the measured enzyme concentrations in the matrix and the $k_{cat}$ values determined for native enzyme of released enzyme samples. Use of such values would appear reasonable, since: (a) theoretically, the intrinsic value for $k_{cat}$ is approached at high substrate concentrations; and (b) the intrinsic value for the immobilized enzyme appears to be similar to that for the native form, in that the value for soluble, released enzyme (with immobilization chains attached) is similar to that of native enzyme. Identifying the preparation with 20.2 mg α-chymotrypsin per gram with subscript 2 and that with 0.5 mg/g with subscript 1, the value for $$\phi_2/\phi_1 = \frac{r_2}{r_1} \cdot \left[\frac{V'_{max,2}}{V'_{max,1}}\right]^{\frac{1}{2}} = (V'_{max,2}/V'_{max,1})^{\frac{1}{2}}$$

was calculated to be 1.46. Also, values for $V'_{max}/\kappa$, where $\kappa \equiv K_m\epsilon$ were obtained from linear computer fits to both double-reciprocal plots and Hofstee-Eadie plots, for both preparations. The first-order effectiveness factor, $\epsilon$, is defined as $$\epsilon = \frac{1}{\phi}\left[\left[\frac{1}{\tanh 3\phi}\right] - \frac{1}{3\phi}\right]$$

From the values of $\kappa$ obtained, the ratio of $$\frac{\epsilon_2}{\epsilon_1} = \frac{\kappa_1}{\kappa_2}$$

was calculated to be 0.85. From these various ratios a value of $\phi_1 \simeq 5$ was estimated from the relationship given in FIG. 7 by Engasser and Horvath (1973), and, from it, a value for $\phi_2$ of 7.5 was estimated. Using the expression for the substrate modulus (equation 2), values for $K_m$ and $D_{eff}$ can then be calculated for each preparation. The resulting values for $K_m$ are 3.3 mM and 2.5 mM for the preparations with 20.2 mg/g and 9.5 mg/g, respectively. The corresponding values for $D_{eff}$ are $1.4 \times 10^{-5}$ cm$^2$/min and $1.7 \times 10^{-5}$ cm$^2$/min. respectively. Hence the values obtained for $K_m$ are in rather good agreement with that for the native enzyme. Also, the values for $D_{eff}$ appear to be reasonable in comparison to values reported for other substrates in gel matrices by Regan, D. L., Lilly, M.D., and Dunnill, P. (1974), *Biotechnol. Bioengr.* 16, 1081–1093. From these results it can be concluded that the reduction in chymotryptic activity following immobilization to porous glass particles can be entirely accounted for by pore diffusional inhibition.

BRIEF DESCRIPTION OF THE DRAWINGS

▲, △: 20.2 mg enzyme per gram of glass.

■, □: 9.5 mg enzyme per gram of glass.

Solid lines are least squares fits of the points to a hyperbola.

Each point is the mean of two measurements.

The methods and results set forth hereinafter are offered to more fully illustrate the present invention, but are not to be construed as limiting the scope thereof.

METHODS

α-Chymotrypsin (EC 3.4.21.1) from bovine pancreas was obtained as a lyophilized powder from Miles Laboratories or Sigma Chemical Co. and used without further purification. All chemicals used were reagent grade or better.

Protein was immobilized on the surface of porous glass beads (obtained from Sigma Chemical Co.) by covalent binding via succinamidopropyl-silane chains. Beads were cleaned with concentrated nitric acid in a boiling water bath for 1 hour, then rinsed until the pH reached 7.0. The beads were silanized and succinylated as described by Cho, I. C., and Swaisgood, H. (1974), *Biochim. Biophys. Acta* 334, 243–256, the contents of which are incorporated herein by reference. The succinamidopropyl-glass beads were washed with water, dried in a vacuum oven, then stored dry until needed for protein immobilization. As an indication of completion of the succinylation reaction, a small sample of the beads was treated with 2,4,6-trinitrobenzenesulfonate. Absence of red-orange color was taken as evidence of near completion of the reaction in a manner described by Cuatrecasas, P. (1970b), *J. Biol. Chem.* 245, 3059–3065, the contents of which are incorporated herein by reference. The number of chains immobilized per gram of glass was measured by quantitation of nitrogen using the micro-Kjeldahl-microdiffusion technique described by Janolino, V. G., and Swaisgood, H. E. (1975), *J. Biol. Chem.* 250, 2532–2538, the contents of which are incorporated herein by reference.

Succinamidopropyl-derivatized glass was converted to the acyl chloride derivative by treatment with anhydrous thionyl chloride. Care was taken to prevent the introduction of water in each of these reaction steps. The reacion mixture was held at 70° C. for 1 hour. The solution was then cooled to 25° C., and excess thionyl chloride was drained from the beads, which were then rinsed thoroughly with dry dichloromethane. The beads were next covered with anhydrous 3-mercaptopropionic acid and again held at 70° C. for 1 hour. Following reaction, the excess acid was drained, and the derivatized beads were again washed with dichloromethane. After thorough drying at 125° C. in a vacuum oven, the beads were stored in the absence of solvent until needed for protein attachment.

Protein attachment to the thioester beads was achieved by degassing the beads in buffer, then recycling protein solution through the beads in a fluidized bed configuration for several hours. To determine the amount of protein immobilized, all protein not covalently bound to the beads was removed before amino acid analysis by rinsing with (per gram of beads) 1.2 liters H$_2$O (or 0.1 ionic strength phosphate buffer), then with 400 ml 3.3 M urea made 0.01 M in imidazole, followed by 1.2 liters buffer. Samples of beads were subjected to hydrolysis in 6 N hydrochloric acid at 110° C. for 24 hours. Either a Beckman 116 or a Durrum 500 amino acid analyzer was used for the analysis; both were equipped with peak-integrating computers.

A portion of the immobilized protein was released from the matrix by cleavage of the thioester bond with a solution of 1.0 M hydroxylamine (pH 7.0) at room temperature.

Hydrolysis of benzoly-L-tyrosine ethyl ester (BzTyrOEt) by α-chymotrypsin was assayed according to the method of Hummel, B. C. W. (1959), *Can. J. Biochem. Physiol.* 37, 1393–1399, the contents of which are incorporated herein by reference. Reaction was initiated by addition of soluble enzyme to the reaction mixture, and reaction progress was monitored spectrophotometrically at 256 nm. In the case of immobilized enzyme, all reactants except the substrate were recycled through the beads and the reaction was initiated by addition of BzTyrOEt. Conversion of less than 2% of the substrate to product per pass through the beads allows the use of differential kinetics as described by Ford, J. R., Lambert, A. H., Cohen, W., and Chambers, R. P. (1972), *Biotechnol. Bioeng. Symp. No.* 3, 267–284, contents of which are incorporated herein by reference. These conditions were achieved by recycling a volume of 20 ml through less than 0.05 μmol of immobilized enzyme. BzTyrOEt concentrations were varied from 7.0 μM to 1.65 mM where the limit of measurement by the spectrophotometer was reached. Initial slopes were read directly from the recorder chart and kinetic constants were evaluated using a computer program to fit data directly to velocity versus substrate concentration curves.

Ellman's procedure was used for determination of total sulfhydryl groups in proteins (Ellman, G. L. (1959), *Arch. Biochem. Biophys.* 82, 70–77 and Kalab, M. (1970), *J. Dairy Sci.* 53, 711, 718, contents of each are incorporated herein by reference). Urea was used as a denaturant to expose buried sulfhydryl groups before samples were assayed.

Samples were prepared for mass spectrometry using a rotary evaporator to remove most of the moisture, and then freeze-dried. High resolution mass spectra were obtained. All calculations and predicted structures were verified by computer analysis.

RESULTS

All of these studies were performed using 120/200 mesh size porous glass beads (1100 Å mean pore diameter) which were derivatized with succinamidopropyl chains at a level of 88 μmoles N per g. The thioester derivative was prepared and at first, immobilization of protein was attempted by activating the carboxyl groups of the mercapto-acid termini of the convalently attached chains using a water-soluble carbodiimide (EDC). Surprisingly, however, such activation of carboxyl groups was found to be unnecessary. Indeed, under the conditions used, treating the beads with EDC prior to exposure to protein resulted in only 20% as much protein immobilized as when protein was added directly to the thioester derivatized glass as illustrated in Table I.

TABLE I

Covalent Immobilization and Release of α-Chymotryps in from Thioester-Derivatized Glass Beads

| | mg α-Chymotyrpsin Bound[a] g Glass | | |
|---|---|---|---|
| | Before 1 M NH$_2$OH | After 1 M NH$_2$OH | % Released |
| "non-activated" | 20.9 | 6.3 | 69.9 |
| EDC-"activated" | 4.4 | 4.1 | 6.8 |

[a]Solutions containing 1 mg/ml enzyme at pH 7.0 were recycled through both types of beads for three hours. Half of each sample was rinsed with 1 M NH$_2$OH. Prior to amino acid analysis, all samples were rinsed thoroughly with 3.3 M urea, 0.01 M imidazole and water.

Figure 1:
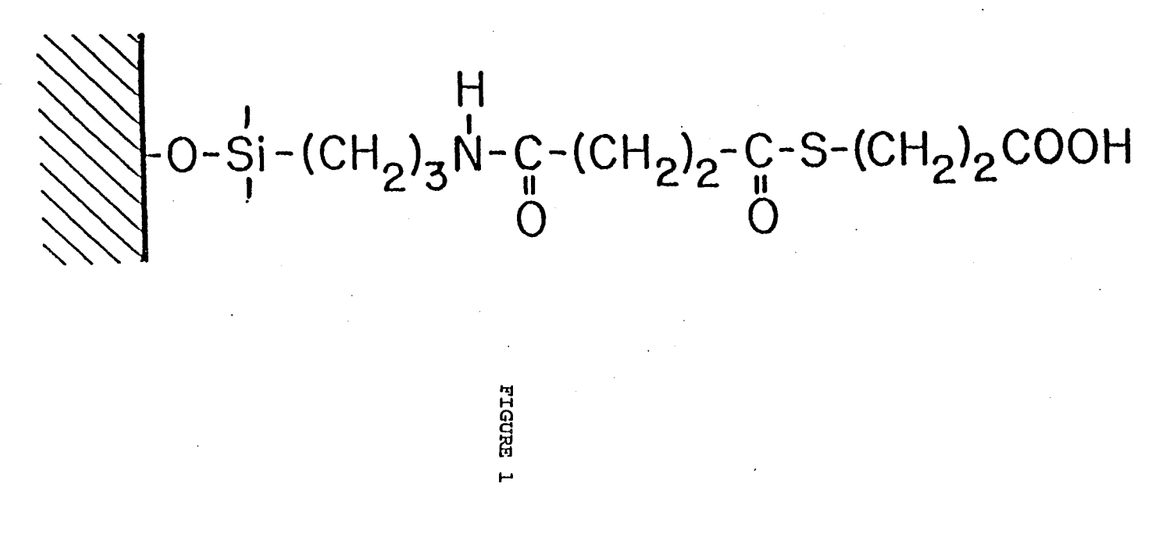
FIG. 1 is a postulated structure of the thioester-glass derivative.

Following thioester derivatization, the beads become distinctly yellow to yellow-orange in color. The electronic absorption spectrum, obtained by placing the glass beads in carbon tetrachloride, which has a refractive index close to that of glass, indicated a broad absorption maximum centered around 400 nm. A high resolution mass spectrum was obtained for the cleavage products resulting from 24-hour hydrolysis in 6 N HCl. The largest fragment had a mass of 207.0319. Calculations (based on carbon twelve with all other atoms as their most abundant isotopes) predict a value of 207.0326 for the molecular mass plus one of S-succinylmercaptopropionic acid. These results support the contention that a thioester derivative, as indicated in FIG. 1, had been formed on the glass surface.

To investigate the identity of the amino acid residue(s) which react with the thioester-derivatized beads, a number of model compounds, in which all but one of the functional groups were blocked, were exposed to the beads under immobilization conditions. The results, given in Table II below, show that compounds having either a free α- or ε-amino group reacted to give a covalently immobilized derivative. The amounts immobilized would correspond to about 15 mg of α-chymotrypsin per g glass, assuming one site of attachment per protein molecule.

TABLE II

Model Compounds Tested for Reactivity with Thioester Derivatized Glass Beads

| Compound | Functional Group Available | Amount Bound (μmole/g)[a] |
|---|---|---|
| α-N-Benzoyl-L-arginine ethyl ester | guanidino | 0 |
| α-N(p-Tosyl)-L-arginine methyl ester | guanidino | 0 |
| α-N-Acetyl-L-lysine methyl ester | ε-amino | 0.4 |
| α-N-Acetylhistamine | imidazole | 0 |
| N-Acetyl-L-tyrosine ethyl ester | phenolic | ND[b] |
| Glycine ethyl ester | α-amino | 0.6 |

Figure 2:
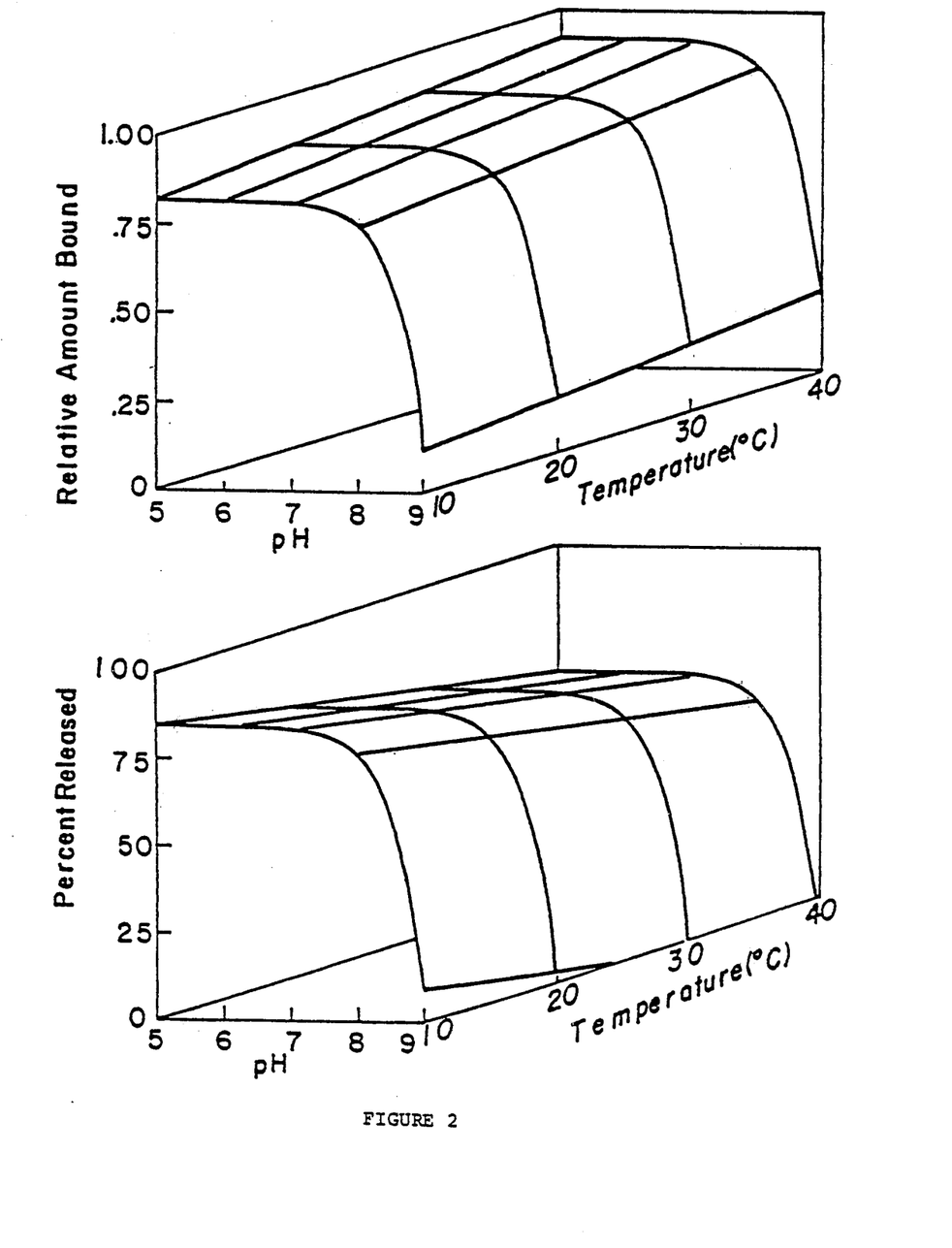
FIG. 2 represents prediction surfaces for binding and release of protein on thioester-derivatized glass as a function of pH and temperature.

[a]Determined by amino acid analysis following thorough washing with 4 M urea, 0.01 M imidazole, then water to remove substances not covalently bound.
[b]Not determinable because the thioester derivative yields, upon amino acid analysis, a peak overlapping the position of tyrosine. (Seemingly none was bound, based on the data given in FIG. 2 and the $pK_a$ of tyrosine's hydroxyl group.)

Covalent immobilization of compounds which leave the thioester bond intact should yield derivatives which could be released in 1 M hydroxylamine. Furthermore, the released derivative should contain one sulfhydryl group for each site of attachment. α-Chymotrypsin, which had been immobilized by this procedure, was released by washing the beads with 1 M hydroxylamine, and isolated by concentrating the solution containing the enzyme by ultrafiltration through an Amicon PM 10 membrane. Measurement of the free sulfydryl groups on the released protein gave an average 3.3 mols per mol of protein. Also, during the release reaction, formation of gas bubbles was observed in the reaction mixture.

To establish the optimum conditions for immobilization with respect to both the amount of protein immobilized and the amount which could be subsequently released in hydroxylamine, experiments were performed in which the pH and temperature of the immobilization reaction were varied. Thus, α-chymotrypsin was immobilized using a three-hour reaction period at pH values ranging from 5 through 9 and temperatures of 10°, 25°, and 40° C. Each immobilized enzyme sample was divided into two portions, one of which was washed with 1 M hydroxylamine (pH 7.0). All samples were washed with 3.3 M urea, 0.01 M imidazole and water prior to amino acid analysis. Statistical least-squares analysis of the results produced the surfaces shown in FIG. 2. Relationships shown are significant with a probability level of $P<0.0001$ with $R^2=0.73$. Increasing the pH between 5 and 8 did not greatly affect the amount of protein immobilized; however, above pH 8 the amount was dramatically reduced. Although increasing the temperature also increased the amount immobilized, it appeared to decrease the percentage which could be subsequently released by treatment with 1 M hydroxylamine.

Both the storage stability of the thioester-glass derivative and that of the covalent protein attachment were investigated. Derivatized beads were held dry at room temperature for six months between preparation and protein immobilization without affecting their capacity to both bind and release protein. After immobilization, samples of α-chymotrypsin-beads were rinsed and held in one of the following solvents (in the presence of 0.02% sodium azide) at room temperature for one month: sodium phosphate solutions of pH 5.0, 7.0, and 9.0, respectively; 6 M guanidinium chloride; and distilled water. Following storage, the samples were divided into aliquots, half of which were treated with 1 M urea and water in preparation for amino acid analysis. Results, listed in Table III below, indicate no significant loss of protein during storage, except for that in guanidinium chloride. However, the percentage releasable appeared to decrease as a result of storage for one month.

TABLE III

Effects of Various Storage Conditions on Thioester-Immobilized Protein[a]

| | mg Protein/g Beads | | % Release |
|---|---|---|---|
| Solvent | Before 1 M NH$_2$OH | After 1 M NH$_2$OH | |
| Distilled Water | 12.9 | 9.9 | 23 |
| 6 M Guanidinium chloride | 9.6 | 9.4 | 2 |
| pH 5 Sodium phosphate | 14.2 | 11.7 | 18 |
| pH 7 Sodium phosphate | 14.0 | 12.2 | 13 |
| pH 9 Sodium phosphate | 12.7 | 11.2 | 12 |
| Not stored | 14.0 | 8.1 | 42 |

[a]All stored samples were allowed to stand at room temperature for one month.

The effect of chain length in the thiol acid attached to the glass surface was investigated. 2-Mercaptoacetic acid, like 3-mercaptopropionic acid, produced a reactive surface derivative. Thus, shortening the chain by one methylene group did not significantly affect the amount of protein which could be immobilized. However, there appeared to be an increase in the amount subsequently released with hydroxylamine (as shown in Table IV below).

TABLE IV

Effects of Binding and Removal of Protein Caused by Variation of Chain Length in the Thioester Procedure

| Parameter | HS(CH$_2$)$_2$COOH | HSCH$_2$COOH |
|---|---|---|
| Protein Bound (mg/g Beads) | 14.0 | 16.4 |
| Protein Removed (mg/g Beads)[a] | 5.9 | 11.6 |
| Percent Removed | 42.3 | 70.5 |

[a]Protein was removed by washing with a M hydroxylamine at pH 7 and room temperature. All samples were washed with 3.3 M urea, 0.01 M imidazole and distilled water prior to amino acid analysis.

The effects of immobilization on the kinetic parameters of α-chymotrypsin were investigated using the techniques described above for immobilization and release of the enzyme. As shown by the data given in Table V below, the measured parameters for the native soluble enzyme and the released enzyme samples did not differ significantly. Hence, the covalent linkage(s) of the enzyme to the coupling chain(s) per se, did not appear to critically modify the conformation or sterically hinder access to the catalytic site, so as to alter the kinetic constants of those enzyme molecules which were subsequently released. These kinetic studies were performed using conditions which should have minimized external diffusion effects; therefore, the observed dramatic changes in the kinetics of the immobilized enzyme preparation are most likely the result of internal diffusion limitations.

TABLE V

Kinetic Parameters of α-Chymotrypsin

| Enzyme Preparation | $K_m$(app) (mM) | $k_{cat}$ (sec$^{-1}$) | $k_{cat}/K_m$(app) (mM$^{-1}$ sec$^{-1}$) |
|---|---|---|---|
| Soluble enzyme before immobilization | 2.74 ± 0.72 | 54.4 ± 9.0 | 19.9 |
| Immobilized (20.2 mg/g) | 4.43 ± 2.46 | 3.9 ± 1.7 | 0.9 |

TABLE V-continued

| Kinetic Parameters of α-Chymotrypsin | | | |
|---|---|---|---|
| Enzyme Preparation | $K_m$(app) (mM) | $k_{cat}$ (sec$^{-1}$) | $k_{cat}/K_m$(app) (mM$^{-1}$ sec$^{-1}$) |
| Immobilized (9.5 mg/g)$^a$ | 6.69 ± 2.02 | 6.9 ± 1.7 | 1.0 |
| Soluble enzyme released by hydroxylamine | 3.35 ± 0.68 | 64.3 ± 8.8 | 19.2 |

$^a$The same immobilized enzyme preparation (20.2 mg/g) after brief treatment with 1 M hydroxylamine.

Effects of internal diffusion in a spherical particle have been quantitatively described by the relationship (see Engasser, J. M., and Horvath, C. (1973), *J. Theor. Biol.* 42, 137–155 and Goldstein, L. (1976), *Methods Enzymol.* 44, 397–443) the contents of each being incorporated herein by reference $$\frac{d^2\sigma}{dl^2} + \frac{2}{l} \cdot \frac{d\sigma}{dl} = \phi^2 \left( \frac{\sigma}{1+\sigma} \right) \quad (1)$$

where $\sigma$ is the dimensionless concentration ratio within the pore volume (given by $[S]/K_m$), $l$ is the dimensionless distance, and the Thiele modulus, $\phi$, is given by $$\phi = \frac{r}{3} \sqrt{\frac{V'_{max}}{K_m D_{eff}}} \quad (2)$$

where $r$ is the particle radius, $V_{max}'$ is the saturation velocity per unit volume of catalyst, and $D_{eff}$ is the effective diffusion coefficient for substrate within the matrix. Departure of the observed rate from the kinetic rate can be expressed in terms of an effectiveness factor, $\eta$:

$$v' = \eta V_{kin}' \quad (3)$$

Equation (1) can be integrated numerically to give a calculated rate for the catalyst particle and, thus, graphical relationships between the effectiveness factor, $\eta$, the Thiele modulus $\phi$, and the dimensionless concentration $\sigma$.

Figure 3:
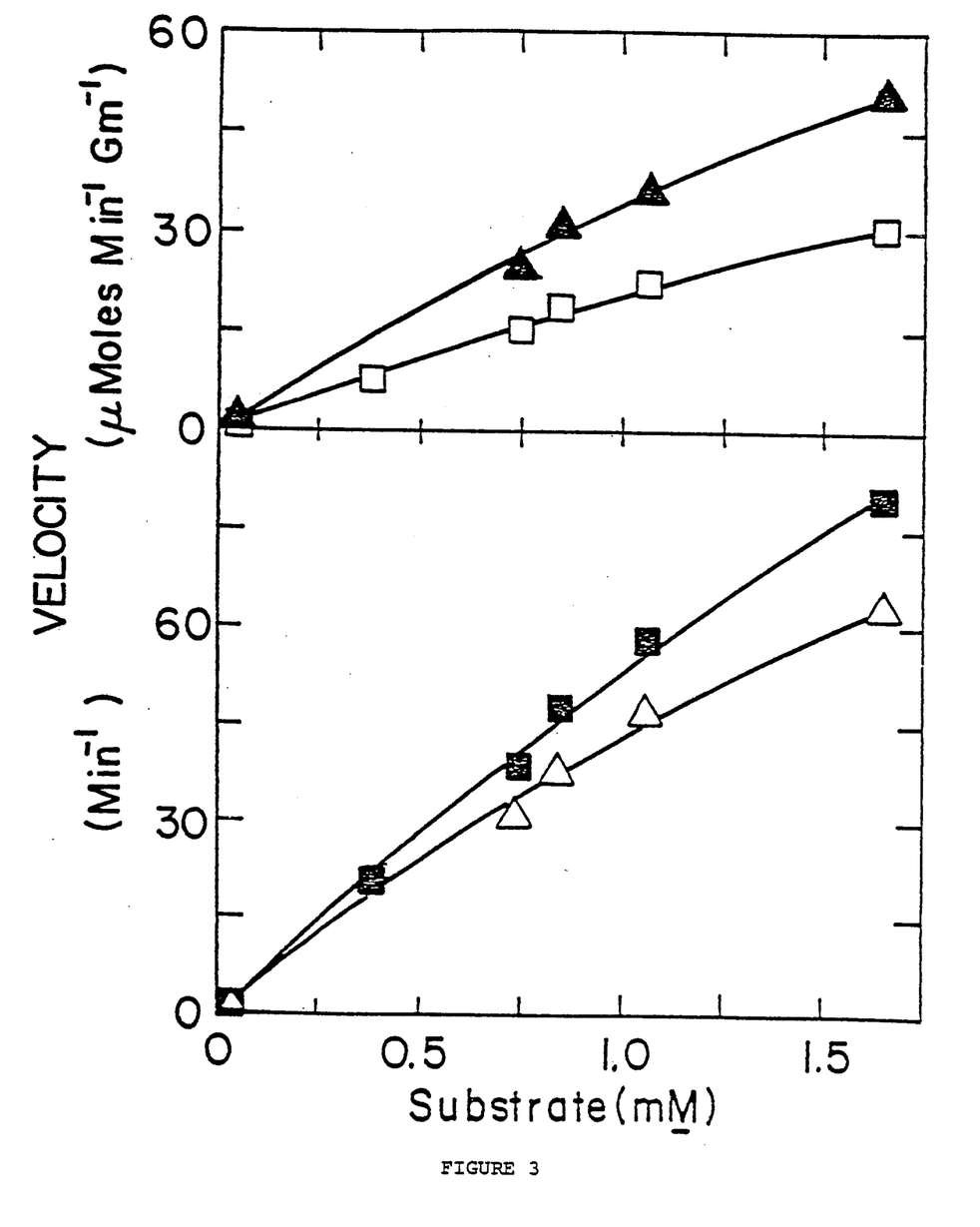
FIG. 3 illustrates the effect of releasing a portion of the α-chymotrypsin from thioester-glass beads on the total and specific activity. Top: activity per gram of glass. Bottom: activity per mole of enzyme.

In our case, substrate concentrations were limited to values of $\sigma \leq 0.55$. Therefore, all of the measurements were made under conditions approaching first order, as exemplified by the near linearity of the observed rates as a function of substrate concentration as illustrated by FIG. 3. Consequently, the saturation rate, $V_{max}'$, could not be experimentally obtained. However, as expected for the case of diffusional limitations, removal of roughly one-half of the enzyme (by treatment with hydroxylamine) resulted in an increase in the specific activity for the remaining enzyme immobilized as shown in FIG. 3 (lower curves). Comparison of the extrapolated values for the $k_{cat}/K_m$ ratio for soluble and immobilized enzymes yields a first-order effectiveness factor of roughly 0.05 for the preparation containing 20 mg enzyme/g.

Amino acid analysis of thioester-derivatized beads which had been incubated with protein or model amino acid derivatives and subsequently washed with denaturants under conditions shown to remove all adsorbed material, clearly demonstrated that such beads were capable of covalently immobilizing protein without the addition of carbodiimide. Because of the mild conditions and fairly wide range in pH and salt concentration which are compatible with the immobilization reaction, our method appears very attractive for attachment of biologically active proteins to solid surfaces. Furthermore, thioester-derivatized beads remain stable for long periods of time and the immobilization procedure simply requires incubation of a solution containing the protein with the thioester-glass derivative. It should be noted that there is no exposure of the protein to immobilization reagents, such as CNBr or EDC, in solution, thereby minimizing undesirable side reactions, protein cross-linking, and secondary chemical modifications.

While the invention has been described as above, it is clear that variations can be made thereto without departing from the spirit and scope thereof. Thus, the invention may comprise, consist, or consist essentially of the various steps and materials recited herein.

We claim:

1. A reversible method for the covalent immobilization of proteins which comprises:
   a. treating an inorganic oxide material to provide an activated surface thereon by the steps of:
      i. silanizing and succinylating the inorganic oxide material to provide a succinamidopropyl-surface;
      ii. converting the succinamidopropyl-surface to the acyl chloride derivative by treatment with thionyl chloride under anhydrous conditions; and
      iii. reacting the acyl chloride derivative with either 3-mercaptopropionic acid or mercaptoacetic acid under anhydrous conditions, whereby the surface of said inorganic oxide material is activated; and
   b. contacting the activated surface with protein having a reactive amino group whereby said protein is covalently bonded to the activated surface.

2. A method according to claim 1 wherein the inorganic oxide material having an activated surface is dried prior to contacting with said protein.

3. A method according to claim 1 wherein the contacting of proteins with the activated surface is carried out at a pH ranging from about 5 to 8.

4. A method according to claims 1, 2 of 3 wherein said inorganic oxide material is selected from the group consisting of porous glass beads and porous silica.

5. A method according to claim 4 wherein the inorganic oxide material having an activated surface is suspended in a buffer and said contacting is effected by recycling a solution of the protein through the suspended material.

6. A method according to claim 1 wherein the covalently bonded protein is treated with hydroxylamine whereby said protein is mobilized by cleavage from the activated surface.

7. A method according to claims 1, 2 or 3 wherein said inorganic oxide material is siliceous.

8. A method for preparing a material having an activated surface suitable for the reversible immobilization of enzymes or proteins thereon which comprises:
   a. silanizing and succinylating an inorganic oxide material to provide a succinamidopropyl-surface;
   b. converting the succinamidopropyl-surface to the acyl chloride derivative by treatment with thionyl chloride under anhydrous conditions;
   c. reacting the acyl chloride derivative with either 3-mercaptopropionic acid or mercaptoacetic acid under anhydrous conditions whereby the surface of said material is activated; and
   d. drying the activated material.

9. A process according to claim 8 wherein said material is siliceous and is selected from the group consisting of porous glass beads and porous silica.

10. A siliceous material having an activated surface, said material having been prepared according to the process of claims 8 or 9.

* * * * *